(12) United States Patent
Antonio

(10) Patent No.: US 11,305,139 B2
(45) Date of Patent: Apr. 19, 2022

(54) COMBINATION COMPACT PELVIC BINDER AND CLIMBING HARNESS

(71) Applicant: Ishmael L. Antonio, Rio Rancho, NM (US)

(72) Inventor: Ishmael L. Antonio, Rio Rancho, NM (US)

(*) Notice: Subject to any disclaimer, the term of this patent is extended or adjusted under 35 U.S.C. 154(b) by 404 days.

(21) Appl. No.: 16/448,733

(22) Filed: Jun. 21, 2019

(65) Prior Publication Data

US 2020/0009411 A1    Jan. 9, 2020

Related U.S. Application Data

(60) Provisional application No. 62/688,348, filed on Jun. 21, 2018.

(51) Int. Cl.
*A62B 35/00* (2006.01)
*A61B 17/132* (2006.01)

(52) U.S. Cl.
CPC ...... *A62B 35/0012* (2013.01); *A61B 17/1325* (2013.01)

(58) Field of Classification Search
CPC ............ A62B 35/0006; A62B 35/0018; A62B 35/0037; A45F 3/14; A45F 2003/144; A45F 2003/148; A61B 17/1325
See application file for complete search history.

(56) References Cited

U.S. PATENT DOCUMENTS

| | | | |
|---|---|---|---|
| 6,481,528 B2 | 11/2002 | Antonio | |
| 8,192,383 B2* | 6/2012 | Polliack | A61F 5/0193 602/19 |
| 8,926,536 B2 | 1/2015 | Hopman et al. | |
| 9,968,475 B2* | 5/2018 | Ross | A61F 5/34 |
| 10,010,729 B1* | 7/2018 | Murphy | A62B 35/0018 |
| 2001/0047904 A1* | 12/2001 | Antonio | A45F 5/021 182/3 |
| 2004/0140152 A1* | 7/2004 | Richardson | A62B 35/0037 182/3 |
| 2006/0135898 A1* | 6/2006 | Richardson | A61F 5/028 602/19 |
| 2008/0251087 A1* | 10/2008 | Richardson | A61F 5/0193 128/876 |
| 2010/0152770 A1* | 6/2010 | Spencer | A61B 17/1325 606/203 |
| 2010/0179586 A1* | 7/2010 | Ward | A61B 17/1322 606/202 |

(Continued)

OTHER PUBLICATIONS

SAM Pelvic Sling II, The Seaberg Company, Inc. d/b/a "SAM Medical Products," Pelvic sling offered at https//www.sammedical.com/; last viewed Oct. 25, 2021.

*Primary Examiner* — Brian D Mattei
*Assistant Examiner* — Kathleen M. McFarland
(74) *Attorney, Agent, or Firm* — Rod D. Baker

(57) ABSTRACT

An apparatus and method for providing a pelvic binder in operative combination with a climbing harness. Thigh loop strap portions of a climbing harness system are detachable from the harness belt portion for separate alternative use as an emergency pelvic binder for a patient suspected or diagnosed with pelvic fracture. The thigh strap portions are provided with features and components to facilitate its use as a functional pelvic binder, while nevertheless allowing it to serve as a component of a climbing harness in alternative, ordinary, use.

4 Claims, 9 Drawing Sheets

(56) References Cited

U.S. PATENT DOCUMENTS

| | | | |
|---|---|---|---|
| 2010/0300802 A1* | 12/2010 | Kopp | A62B 35/0037 |
| | | | 182/3 |
| 2012/0245500 A1* | 9/2012 | Polliack | A61F 5/05825 |
| | | | 602/18 |
| 2013/0324898 A1* | 12/2013 | Polliack | A61F 5/0193 |
| | | | 602/18 |

* cited by examiner

COMBINATION COMPACT PELVIC BINDER AND CLIMBING HARNESS

CROSS-REFERENCE TO RELATED APPLICATIONS

This application claims the benefit of the filing of U.S. Provisional Patent Application Ser. No. 62/688,348 titled "Combination Compact Pelvic Binder and Climbing Harness," filed on 21 Jun. 2018, the specification of which is incorporated herein by reference.

BACKGROUND OF THE INVENTION

Field of the Invention

This invention relates generally to medical pelvic binders, and specifically to a type of climbing or tactical harness system adaptable for use as an emergency pelvic binder.

Background

To conduct high angle (steep climb and down rappel) climbing operations, such as in mountaineering and rock climbing, but also including in tactical assaults or rescues in buildings, users (climbers, rescue technicians, tactical operators, law enforcement, etc.) wear a climbing harness system with leg loops. Climbing harness systems have been devised for use by recreational climbers, as well as for use by military and law enforcement personnel. Similar requirements arise in the event of urban assaults, searches, and rescues on cliffs or steep mountainous terrain. To perform high angle maneuvers using climbing ropes, a user must be equipped with some sort of climbing harness by which the user removably and controllably engages with the climbing rope or ropes deployed in the operation. A known type of harness system is disclosed in U.S. Pat. No. 6,481,528 to Antonio, the teachings of which are incorporated herein by reference.

Under many circumstances when a climbing harness is in use, there is potential for encountering personal injury, to the user or a colleague climber, or to another person being rescued. Indeed, in some rescue situations, the user's overriding goal is to reach an injured person to provide first aid. Personal injuries may include a fractured pelvis (or at least a preliminary diagnosis of such). Accordingly, it is highly desirable for a user always to have at the ready an emergency pelvic binder. Presently there is no integrated harness and pelvic binder known to be available.

Stabilizing a suspected pelvic fracture is important first aid which potentially can be applied in the field. Continued movement of an unstable pelvic fracture is likely to result in additional injury. Prompt control of life-threatening bleeding is a paramount goal of on-scene emergency treatment.

A leading treatment goal thus is to stabilize any suspected fractured pelvis. A suitable circumferential pelvic stabilization device preferably should: (1) apply compression so there is less potential space for blood to accumulate in the pelvic cavity; (2) apply pressure against bleeding sources, such as fractured bony surfaces or ruptured vessels; (3) ameliorate instability of the injured pelvis that potentially may further injure tissue, organs, bony surfaces and blood vessels; and (4) reduce the patient's pain by limiting movement of the pelvis.

Pelvic stabilization with a pelvic sheet wrap or mechanical device is indicated for any patient with pelvic instability with unstable or stable vital signs. Stabilization can provide comfort and easier transport. Pelvic compression preferably is undertaken before a patient is extricated. For this reason, it is desirable to have a pelvic binder apparatus in the field, such as in a military, rescue, or law enforcement scenario, including one in which the user has rappelled or climbed to the scene of injury using a climbing belt and harness.

There are known methods to stabilize an injured pelvis. One of the remaining accepted uses for MAST trousers or pneumatic anti-shock garments has been for pelvic fracture stabilization. Other known methods, especially in a controlled environment such as an ambulance or emergency room, include use of a standard hospital draw sheet to create a pelvic sheet wrap, and the SAM® Sling available from the Seaberg Company.

Helpful background information regarding pelvic trauma binders, treatments using such binders, and the general protocols and indications for such are provided by U.S. Pat. No. 9,968,475 to Ross, and U.S. Pat. No. 8,926,536 to Hopman, et al., the disclosures of which are hereby incorporated by reference.

With the foregoing background, the presently disclosed invention was developed. Particularly, there is disclosed a method for using a harness system as a pelvic binder.

SUMMARY OF THE INVENTION

There is disclosed an apparatus and method for providing a pelvic binder in operative combination with a climbing harness. Thigh loop strap portions of a climbing harness system are detachable from the harness belt portion for separate alternative use as an emergency pelvic binder for a patient suspected or diagnosed with pelvic fracture. The thigh strap portions are provided with features and components to facilitate its use as a functional pelvic binder, while nevertheless allowing it to serve as a component of a climbing harness in alternative ordinary use.

BRIEF DESCRIPTION OF THE DRAWINGS

The attached drawings, which form part of this disclosure, are as follows.

Like elements are labeled with like numerals in the several views; the drawings are not necessarily to scale, within a view or relative to each other.

DETAILED DESCRIPTION OF THE INVENTION

Figure 1:
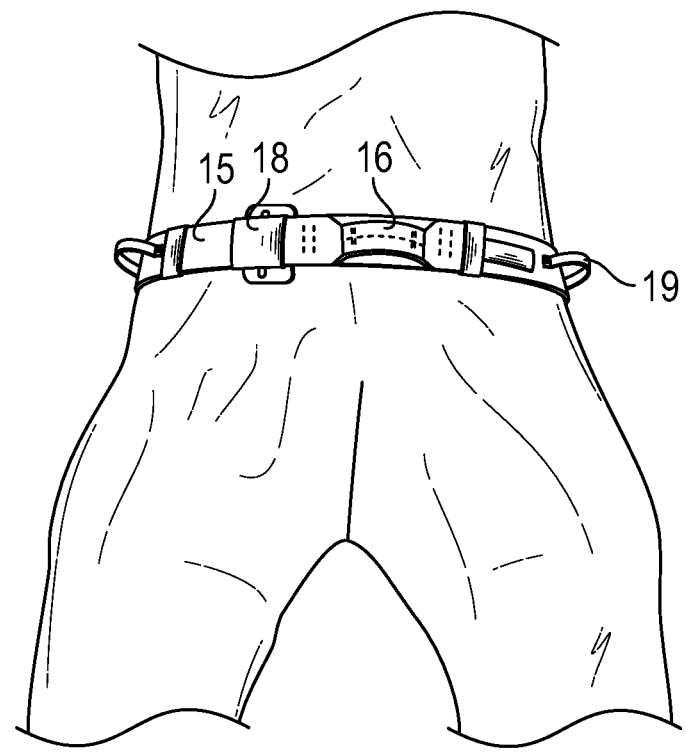
FIG. 1 is a front perspective view of a climbing harness belt, as known generally in the art, and which forms a part of a complete apparatus according to the present disclosure, shown disposed upon the torso of a user.

This invention relates to climbing harnesses, such as those worn by rock climbers, or by law enforcement or military personnel, e.g., when rappelling down a cliff/wall or lowering via a rope from a hovering helicopter. Climbing/rappelling harnesses typically include some sort of waist belt integrated with a pair of thigh straps. Ideally, to simplify and speed use of, as well as assure the ready availability of, a suitable medical pelvic binder, a modular system is provided herein for using a climbing harness as a pelvic binder, such that the binder is always available when the harness system is in use.

Patients with pelvic fractures from high-energy impacts such as a fall from a great height are at risk of fatality from major blood loss. Understanding the anatomy of the pelvis and surrounding structures and the types of pelvic fractures that can occur can help EMS providers recognize and provide in-field stabilization of a pelvic fracture. There are several methods to stabilize a fractured pelvis, but all share the goal of stabilization and reduction.

The pelvis is a ring of paired bones that is the attachment point between a human's upper and lower skeleton. The "pelvic ring" is formed by pairs of fused bones. The pelvis includes the sacral section of the spinal column in the posterior. Attached to each side of the sacrum is an ilium, the upper portion of which is referred to as the iliac crest. On the anterior portion of the pelvis are the pubis and the ischium. The two pubis bones are connected by the symphysis pubis. Many organs and blood vessels pass through, or rest within or near the bones of the pelvis. These include the bladder, urethra, the terminus of the large intestine, and internal reproductive organs. Large blood vessels located in the pelvic ring, when damaged, can be the source of severe bleeding, and large amounts of blood from uncontrolled hemorrhage may accumulate in the spaces within the pelvis. In particular, the right and left iliac arteries descending from the aorta are located in the pelvis. Blood returns from the lower extremities via the right and left iliac veins. Major blood vessels also supply tissue, bones and organs in the pelvic ring. Uncontrolled bleeding is the leading cause of death for patients with a complex pelvic fracture.

The weight of a person's upper body is borne by the pelvis and then transmitted to the legs when the person is standing. A sitting person's weight is borne by the ischium of the pelvis when a person is sitting. The pelvis also protects major blood vessels and organs in the lower abdominal cavity, including parts of the digestive, urinary and reproductive systems. Because the pelvis is the attachment point for numerous muscles that connect the legs to the body, walking, running, standing and many other movements require an intact and stable pelvis.

The disclosed system assures that a pelvic binder is at hand for rapid deployment and use during field operations. According to the system and method, the binder portion also is a component of the harness system. Accordingly, a climber using the present apparatus cannot forget to bring along a suitable pelvic binder, or through complacency or hurry deliberately chose not to bring along a binder, to a climbing or rescue scenario. If the climber is using a harness system according to this disclosure, she automatically has on her person a pelvic binder for use in the event of a medical emergency.

The system according to the present invention includes thigh strap portions, which when in combined use constitute a climbing harness useable in cooperation with a climbing belt. When needed, the straps double in function as a medical pelvic binder according to the further descriptions herein below. Thus, a main aspect of the disclosed invention is the incorporation of pelvic binder features into a climbing harness. For reference to the known art, thigh straps somewhat similar to those seen in my U.S. Pat. No. 6,481,528, may be innovatively modified according to the present disclosure to include elements that enable a climbing harness to function alternatively as a pelvic binder.

In an emergency, the thigh straps can be used as a pelvic binder. In such use, the thigh straps are detached from the load-bearing main belt of the harness, reconfigured for use, and then wrapped around the pelvis. According to the invention, therefore, a user of the climbing harness has a pelvic binder readily at hand as an associated portion (thigh straps) of the harness.

Attention is invited first to FIG. 1, illustrating by way of background a load-bearing climbing harness belt 15 which serves as the main belt portion of a climbing harness system. This main belt 15 is generally according to the prior art and does not form an essential aspect of an apparatus according to the present invention. Rather, it is used in cooperation with the looped harness thigh straps of the invention which can be configured for use as a pelvic binder. It is preferred in the practice of the present invention, however, to provide on the associated belt a sturdy center loop 16. The load bearing belt 15 can be practically any type of climbing harness-type belt known, provided there is a climbing-rated center loop means 16 secured on the belt 15 through which a climbing-rated carabiner may be securely, yet removably, attached to the belt. The belt 15 and loop 16 are both rated according to applicable safety standards for use as weight-bearing climbing harness components. When in use according to this disclosure, the belt 15 is adjusted on the user's torso so that the central loop 16 is situated generally to the center-front of the user's body (i.e., in the general vicinity of the navel, as seen in FIG. 1).

In use, the belt 15 is reliably fastened about the user's body by engaging a free end of the belt with an appropriate buckle (e.g., a ladder buckle or other adequately rated buckle type known in the art of climbing apparatus). The main belt 15 should be suitable for use as a National Fire Protection Association Class 1 harness; combined with appropriate leg loops (thigh straps) discussed hereinafter, the harness system is a Union Internationale des Associations d'Alpinisme (UIAA) rated sit harness (Type C). Various auxiliary loops 19 optionally may be provided on the belt 15 for attachment of gear or the like generally according to convention.

Figure 3:
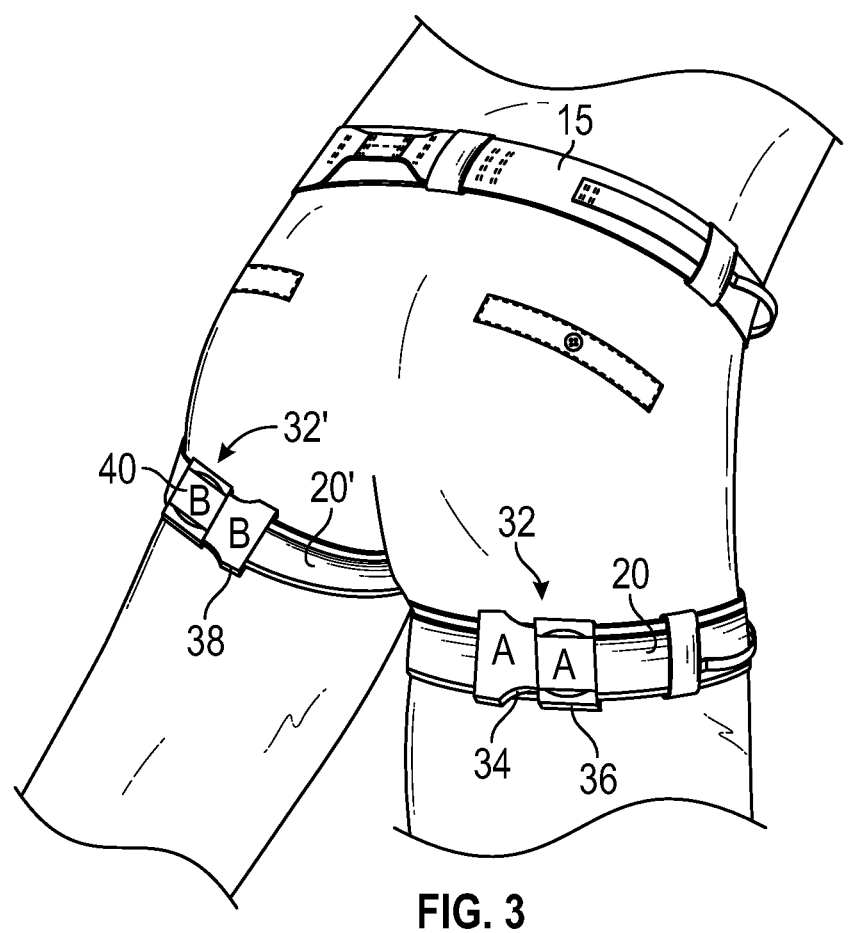
FIG. 3 is a rear view of the looped thigh strap portion of the apparatus according to the present invention according to FIG. 2, shown in a rear view disposed around the thighs of a user.
Figure 4:
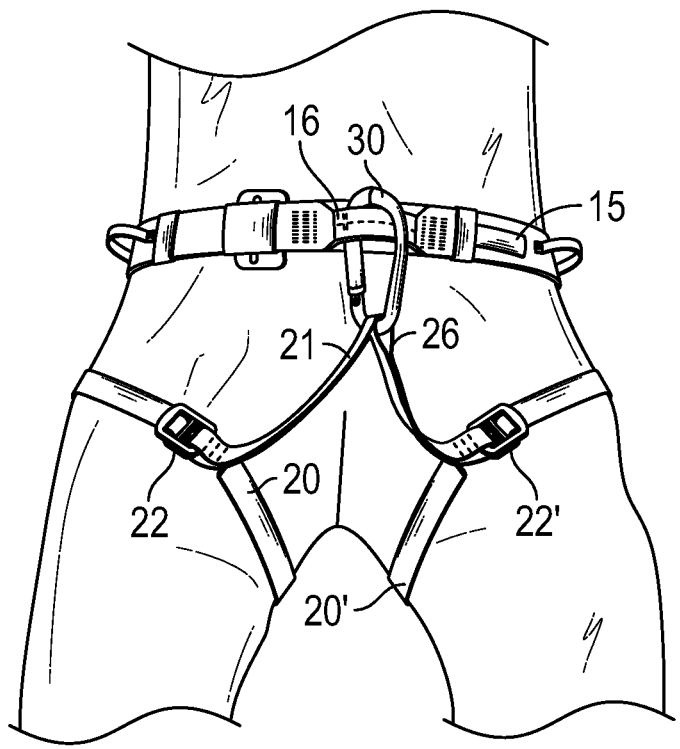
FIG. 4 is a front perspective view of the looped thigh strap portion of the apparatus according to the invention of the present disclosure, shown disposed upon the thighs of a user and connected to a harness belt such as the belt seen upon the user's torso in FIG. 1, the connection by a climbing carabiner.

FIGS. 3 and 4 depict a harness belt 15 as worn by the user of the present system. The harness belt 15 is seen as it would be fitted upon the user at the outset of the practice of the present invention. The belt 15 is wrapped snugly around the user's upper hips, and releasably secured by means of the buckle 18 (FIG. 1). It is noted that the belt is positioned upon the user's body so that the heavy-duty, central, carabiner loop 16 is situated generally centrally at the front of the user's body. A climbing carabiner or other suitable belay device 30 (not seen in FIG. 3) known in the art is releasably attached to the carabiner loop 16 in a manner known in the art for releasably connecting a harness belt to a rope in use for climbing rappelling.

Figure 2:
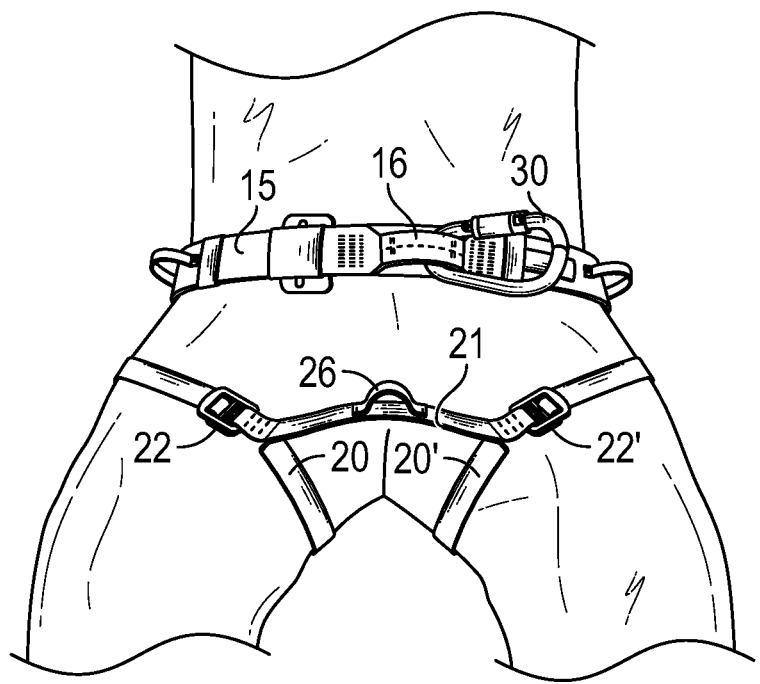
FIG. 2 is a front perspective view of the looped thigh strap portion of the apparatus according to the invention of the present disclosure, shown disposed upon the thighs of a user and detached and unconnected from a harness belt such as the belt seen in FIG. 1.
Figure 6:
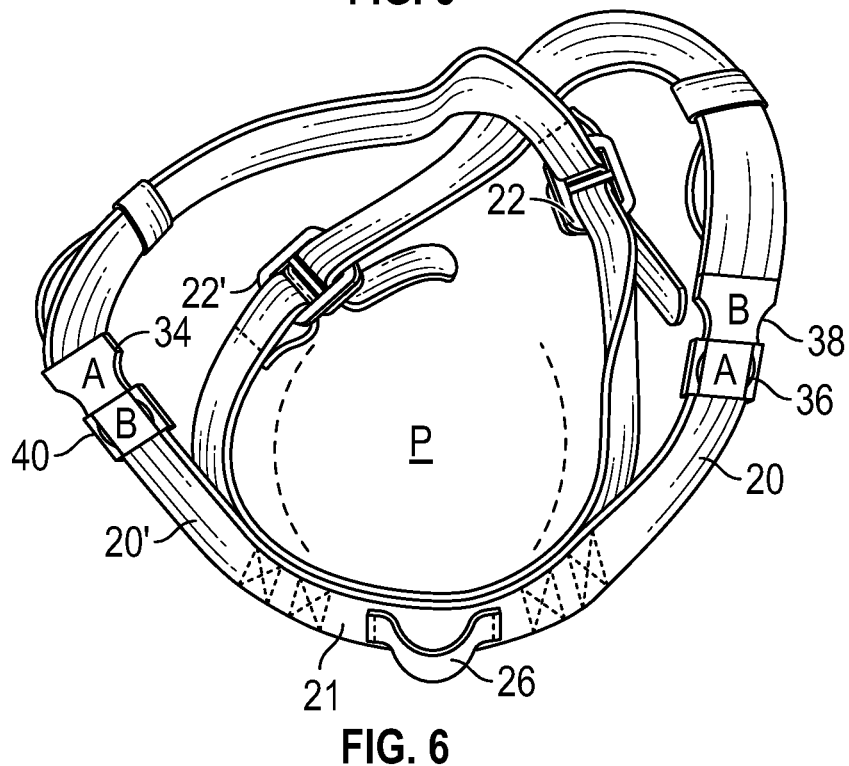
FIG. 6 is a perspective view of the looped harness thigh straps, according to the present disclosure and invention, and shown configured for use as a pelvic binder.

FIGS. 2 and 3 show a thigh strap portion of a harness according to the present disclosure. While this component is referred to as a "thigh strap" or "thigh strap portion" herein, it is to be understood throughout this disclosure that the strap also alternatively serves as a pelvic binder when deployed and used according to the present invention. A UIAA-rated sit harness (Type C) employs two looped thigh straps 20, 20'. In a harness system and method according to the present disclosure, two thigh straps 20, 20' are used, the looped thigh straps are securely joined, as by having ends overlapped and sewn permanently together, by a connecting portion 21. Thus, the connecting portion 21 reliably connects together the looped straps 20, 20' by linking together one end of the first strap 20, and one end of the second strap 20'. Seen in FIGS. 2 and 4 is the carabiner loop 26 that is permanently and reliably secured to or integrated with the connecting portion 21. The carabiner loop 26 is similar to the loop 16 on the belt 15, and is climbing rated. In use during climbing, the straps 20, 20' are looped around respective ones of the user's thighs, and closed by means of respective junction buckles 32, 32' (see FIG. 3). When used as a pelvic binder, the straps 20, 20' are removed from the user's thighs and reconfigured (e.g., as seen in FIG. 6) as disclosed hereinafter.

Figure 5:
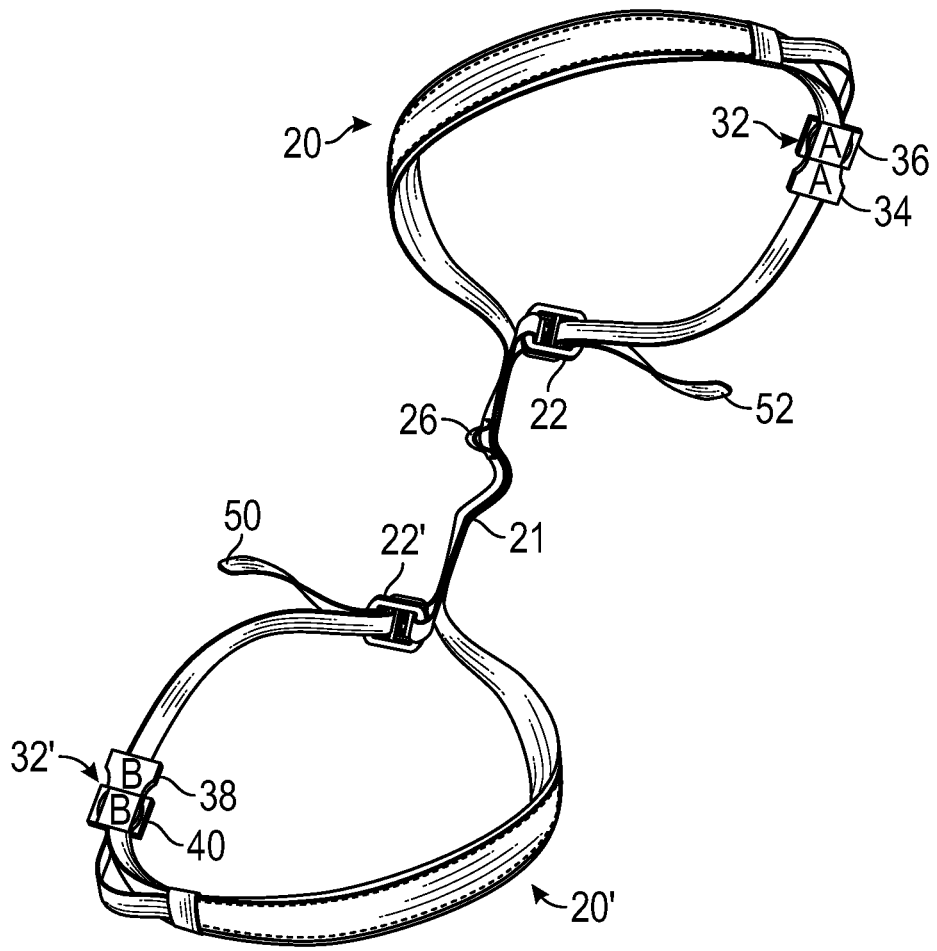
FIG. 5 is a perspective view of the looped harness thigh straps, according to the present disclosure, and shown configured for use as a portion of a climbing harness for placement upon the thighs of a user during harness use.

The thigh straps 20, 20' and their connecting portion 21 are fabricated of nylon webbing, or the like, as known in the art of climbing equipment. Each looped strap 20, 20' may be provided with an associated suitable (climbing equipment rated) adjustment buckle 22, 22' for adjusting (and then releasably fixing) the effective circumference of the loop of the corresponding strap 20 or 20', as disposed around the user's thighs. Manipulation of the adjustment buckles 22, 22' thus permits the user to customize the respective circumferences of the loops of the straps 20, 20' to the sizes of the thighs, thus to snugly wrap and secure the straps 20, 20' to the user when in use in a complete climbing harness system. The buckles 22, 22' preferably are a self-locking type of buckle in common use for harness thigh straps, and may be a COBRA' quick-release buckle available from AustriAlpin, Inc. of Crowsnest Pass, Alberta, Canada. The first or free end 50 or 52 of a thigh strap 20 or 20'can be engaged securely yet releasably with/through a respective buckle 22, 22', as seen in FIG. 5, to secure the thigh strap in the closed condition (FIGS. 2-4) during climbing. Depending upon the particular type of suitable buckle used, the first or free end of a strap 20 or 22' alternatively may also have a second buckling component (not shown in the drawing figures, but known in the art) of a two-part buckling device, for secure engagement with the first buckle part.

Referring jointly to FIGS. 2 and 4, it is seen that the looped thigh straps 20, 20' are attachable and detachable, as a unit, from the climbing belt 15. When the thigh straps 20, 20' are to be used as a component of a climbing harness in use, a climbing carabiner 30 is used to reliably connect the carabiner loop 26 of the thigh straps to the loop 16 on the belt 15. With the straps 20, 20' properly placed in appropriate locations upon the thighs, the climbing carabiner 30 is opened, passed through both loops 16 and 26 and then closed. The combination of the belt 15 and the straps 20, 20' are then configured for use as a climbing harness, as best seen in FIG. 4. The straps 20, 20' may be disconnected from the belt 15 by the simple step of opening the climbing carabiner 30 and releasing the straps 20, 20'; thus disconnected from the belt 15, the detached straps 20, 20' appear as seen in FIG. 2. The detached straps 20, 20' seen in FIG. 2 are then removable from the user's thighs (e.g., by disconnecting the junction buckles 32, 32'), and thus are ready (as seen in FIG. 5) to be reconfigured for use as a pelvic binder.

Placement of the present system for use as a climbing harness thus is illustrated in FIGS. 3 and 4, illustrating how the two thigh straps 20, 20' are disposed upon a user for use. The thigh straps 20, 20' are deployed and re-configured for fulfilling the alternative role of a medical tourniquet. In FIG. 5, each thigh strap 20, 20' is wrapped around the user's upper thigh, in a conventional location. The first or free end 50, 52 of each strap is releasably but securely engaged with its respective strap buckle 22 so that the strap 20 defines a securely closed loop. (See also FIGS. 8 and 10.) The loop 26 can be brought up to the proximity of the carabiner loop 16 on the belt 15, and secured with the carabiner 30, while maintaining a proper positioning of the thigh straps upon the user's thighs.

The rated main carabiner 30 (or other suitable known belay device known in the art) is used to bring and hold together the belt's carabiner center loop 16 and the carabiner loop 26, as seen in FIG. 4. The main carabiner 30 is loopably disposed through loops 16, 26, and closed according to conventional practice. A climbing/rappelling rope (not shown) may then be engaged with/though the carabiner 30 for use in climbing/rappelling, as well-known. When properly installed upon the climber's body for use in climbing/rappelling, the belt 15 and both thigh straps 20 encircle the climber's waist/hips and upper thighs, to provide an appropriate sitting harness.

Attention is returned to FIG. 3. Each of the looped straps 20, 20' is provided with an associated junction buckle 32 and 32'. Suitable junction buckles 32, 32' are known in the art. Junction buckles 32 and 32' connect together ends of the looped the straps. A first junction buckle 32 on the first thigh strap 20 has a first male part 34 securely (per climbing equipment standards) yet releasably engageable with the first female part 36 Engagement of first male part 34 with first female part 36 connects two ends of the first thigh strap 20 when the strap 20 is in use as a component of a climbing harness (e.g., as illustrated in FIGS. 2-4). The first junction buckle 32 may be controllably released by the user, however, to disconnect the ends of the strap 20 that are permanently affixed to respective ones of the parts 34 and 36. Likewise, in the second junction buckle 32' engagement of second male part 38 with second female part 40 connects two ends of the second thigh strap 20' when the second strap 20' is in use as a component of a climbing harness (e.g., as illustrated in FIGS. 2-4). The second junction buckle 32' may be controllably released by the user, however, to disconnect the ends of the second strap 20' that are permanently affixed to respective ones of the parts 38 and 40 of the second junction buckle 32. Thus, when the junction buckles 32, 32' are engaged as seen in FIG. 3, the looped straps 20, 20' are configured for active use in the climbing harness, per FIGS. 1-4.

Reference now is made to FIG. 5. When detached from the harness belt 15 (e.g., by being disconnected from the main carabiner 30), the thigh straps 20, 20' (as connected by the connecting portion 21) have alternative utility as a pelvic binder. FIG. 5 shows the thigh straps 20, 20' as they would appear after being removed from the user's body, but still configured for use within a climbing harness. The thigh straps 20, 20' are joined by the connecting portion 21, which preferably is composed of overlapping lengths of one leg from each of the loops, affixed together as by stitching techniques known in the art. Each loop of each strap is defined by segments of straps whose ends are releasable connected by an adjustable buckle 22 or 22' and a juncture buckle 32 or 32'. FIG. 5 shows the loop of each strap in a harness closed configuration. In the harness closed position the adjustable buckles 22, 22' are engaged. The circumferential length of each loop can be increased/decreased by regulated manipulation of the adjustable buckles 22, 22' by, inter alia, pulling on the free ends 50, 52 of straps as known in the art. Also, in the harness closed configuration, the first male part (A) 34 of first juncture buckle 32 is securely engaged with the first female part (A) 36 of the first juncture buckle 32. Further and as seen in FIG. 5, the second male part (B) 38 of second juncture buckle 32' is securely engaged with the second female part (B) 40 of the second juncture buckle 32'. After removal from the user's body, and as seen in FIG. 5, the thigh straps 20, 20' are ready to be reconfigured, as needed/desired, into a pelvic binder configuration.

Reference is invited to FIG. 6, which illustrates the harness straps 20, 20' arranged in the pelvic binder configuration. To reconfigure from the closed harness configuration of FIG. 5, the two junction buckles 32, 32' are disengaged to open the loops; first male part 34 is released from the first female part 36, and the second male part 38 is released from the second female part 40. If feasible/desired, the two open loops can then be wrapped around the pelvis of the patient, in the manner suggested. The patient's pelvis is situated in the volume P, and if they are not closed already, the two new loops are closed by means of a reversed re-engagement of the juncture buckles 32, 32' as described below.

The two new loops thus configured are disposed adjacently and substantially concentrically in the manner illustrated in FIG. 6, and the harness straps 20, 20' have thus been re-configured for use as a pelvic binder. It is noted that the effective circumferential lengths of the two new strap loops, as seen in FIG. 6, can be adjusted by means of the respective adjustment buckles 22, 22' as needed. The proximally aligned new loops then can be disposed around a patient to function as a pelvic binder. Referring to FIG. 6, the area P inside the two loops is where the patient's pelvis would be situated.

To close the two new loops of the pelvic binder configuration of FIG. 6, the first male part 34 of the first juncture buckle 32 is engaged into and with second female part 40 of the second juncture buckle 32' to define the "new" first loop of strap. The second male part 38 of the second juncture buckle 32' is engaged into and with first female part 36 of the first juncture buckle 32 to define the "new" second loop of thigh strap. This mode of closing the two new loops can be undertaken with the strap segments open, then wrapped around the patient's pelvis (according to medical protocols for binding a fractured pelvis), and then by closing the two loops by engaging male part (A) 34 into female part (B) 40, and male part (B) 38 into female part (A) 36. Alternatively (but typically less desirably) it may be feasible and desirable first to close the two new loops defined by the reversed re-connection of the juncture buckles 32, 32' as described in this paragraph above, and then to dispose the two aligned and closed loops so that the patient's pelvis is disposed within the area P of FIG. 6. The strap loops can be tightened (e.g., using adjustment buckles 22, 22') and compression applied radially inward on the pelvis to stabilize it.

A person skilled in the art of field first aid devices recognizes that the absolute respective lengths of the thigh straps 22, 22' are determined and selected at the time of manufacture/fabrication, so that the effective lengths can be adjusted to function either as harness thigh straps when in the closed harness configuration, or (with increased effective lengths) to have effective circumferences that may correspond to the circumference (in an anatomical transverse plane) of a human patient's pelvis.

Figure 7:
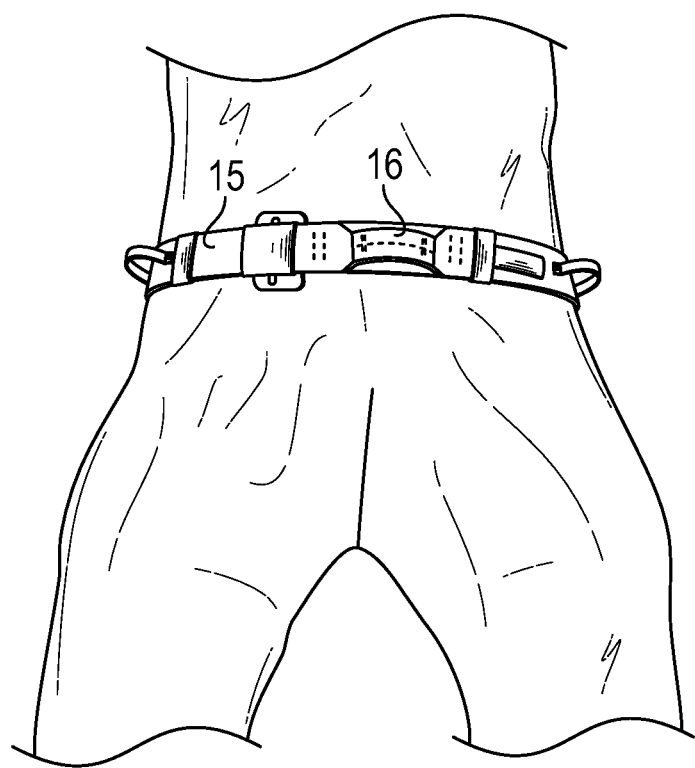
FIG. 7 is a front perspective view of an alternative version of climbing harness belt, according to the present disclosure, shown disposed upon the torso of a user.
Figure 8:
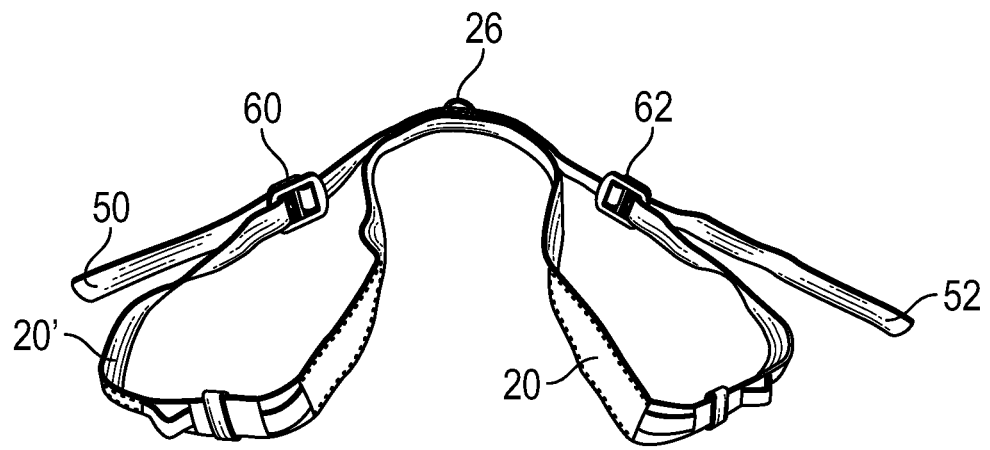
FIG. 8 is a perspective view of an alternative embodiment of looped harness thigh straps, according to the present disclosure, and shown as it would be configured for use as a portion of a climbing harness for placement upon the thighs of a user during harness use, and prior to reconfiguration for alternative use as a pelvic binder.

FIG. 7 is similar to FIG. 1, and depicts a conventional main harness belt 15 upon the torso of a user, as positioned for use in combination with the thigh straps that have double utility as a pelvic binder. FIG. 8, similar in content to FIG. 5 depicts an alternative embodiment of the thigh straps 20, 20' for dual use as a pelvic binder, including the carabiner loop 26 on the connecting portion 21. In this embodiment, the adjustment buckles and the junction buckles seen in previous figures are integrated into binder adjustment buckles 60, 62. The binder adjustment buckles 60, 62 are similar to the adjustment buckles 22, 22' seen in, for example, FIG. 2, but one side of each buckle 60, 62 incorporates a strap ladder slide feature to permit a portion of each thigh strap 20, 20' to be doubled and controllably slipped through a side of each buckle 60, 62 to adjust the effective circumference of each thigh strap loop. Each side component of both binder adjustment buckles 60, 62 is labeled (such as labels (A) and (B) as described hereinabove with respect to FIG. 5), or more preferably color coded, so that the binder adjustment buckles can be used, and reversibly used, as described hereinabove in relation to the juncture buckles 32, 32'.

Figure 9:
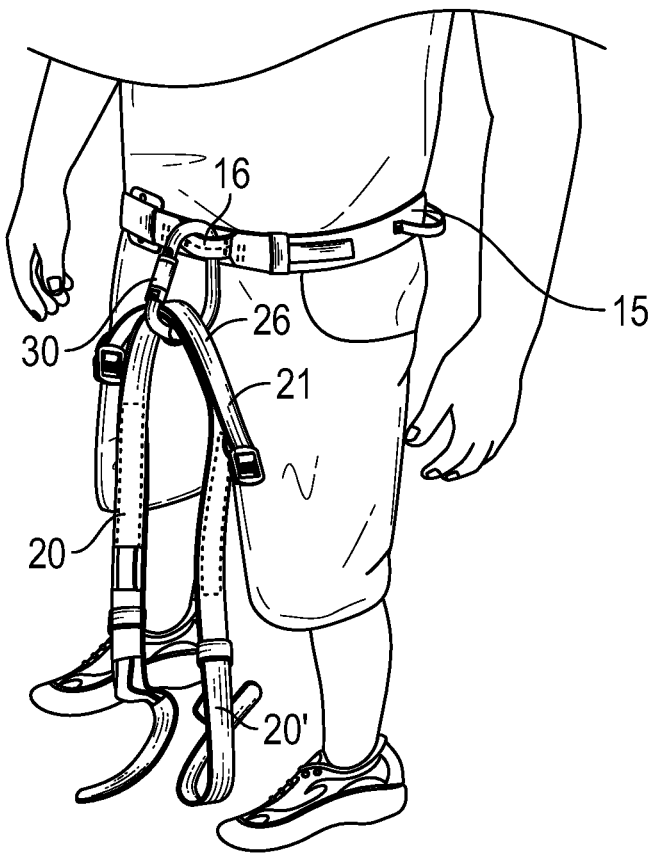
FIG. 9 is a front perspective view of a harness main belt upon the waist of a user, with the thigh strap leg loops hanging from the center loop of the harness main belt.

Further understanding of the practice of an embodiment of the invention may be had with combined reference to FIGS. 9-15. FIG. 9 illustrates how the thigh straps 20, 20' may appear when initially attached to the main belt 50. The belay device or carabiner 30 is disposed through both the main belt center loop 16 and the carabiner loop 26 on the connecting portion of the thigh straps 20, 20'. The straps 20, 20' initially dangle before the user, prior to being stowed around his or her waist.

Figure 10:
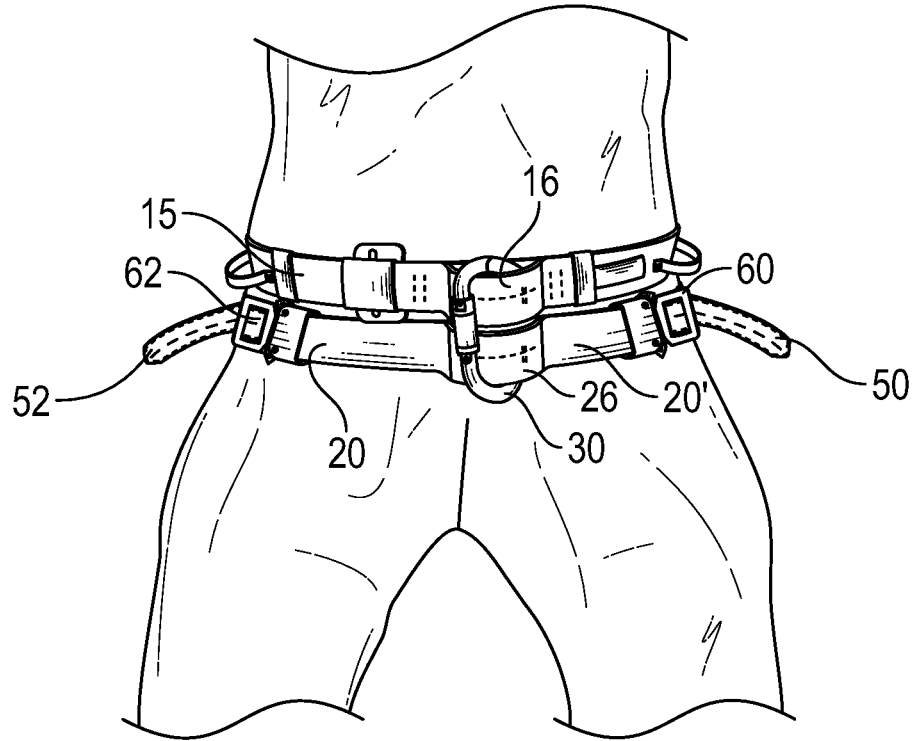
FIG. 10 is a front view of the apparatus and system according to the present invention, with the thigh strap leg loops stowed about the waist of a user while not in active use.
Figure 11:
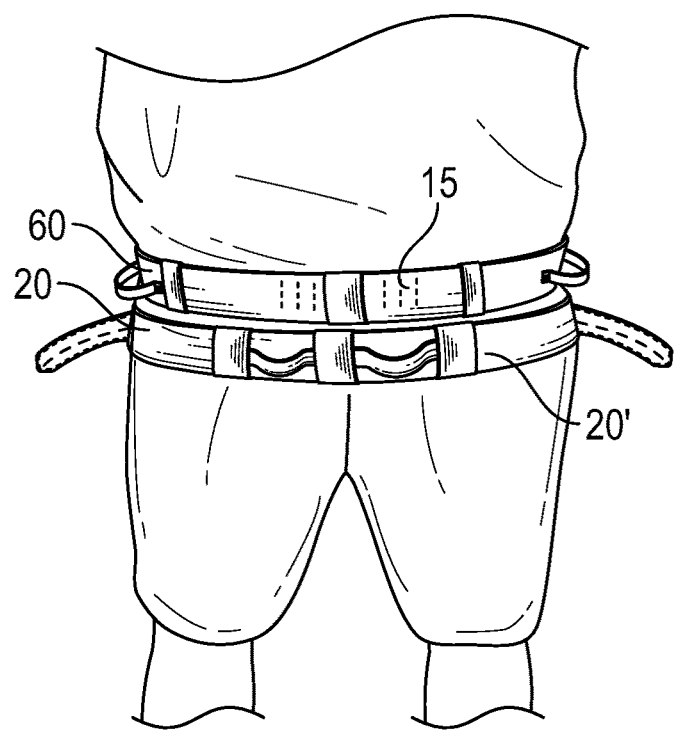
FIG. 11 is a rear view of the apparatus and system according to the present invention, with the thigh strap leg loops stowed about the waist of a user while not in active use.

FIGS. 10 and 11 show that the looped thigh straps 20, 20 can be stowed around the user's waist when not in immediate use for either climbing or as a binder. The binder adjustment buckles 60, 62 have been utilized to expand the effective circumferences of the thigh strap loops, and those loops 20, 20' are wrapped around the user's torso, one on top of the other. The user thus has the thigh straps handy for rapid deployment, either for use as thigh straps in a climbing harness, or alternatively for use as an emergency pelvic binder. The belt center loop 16 and the carabiner loop 26 are both situated at the user's front, as seen in FIG. 10.

Figure 12A:
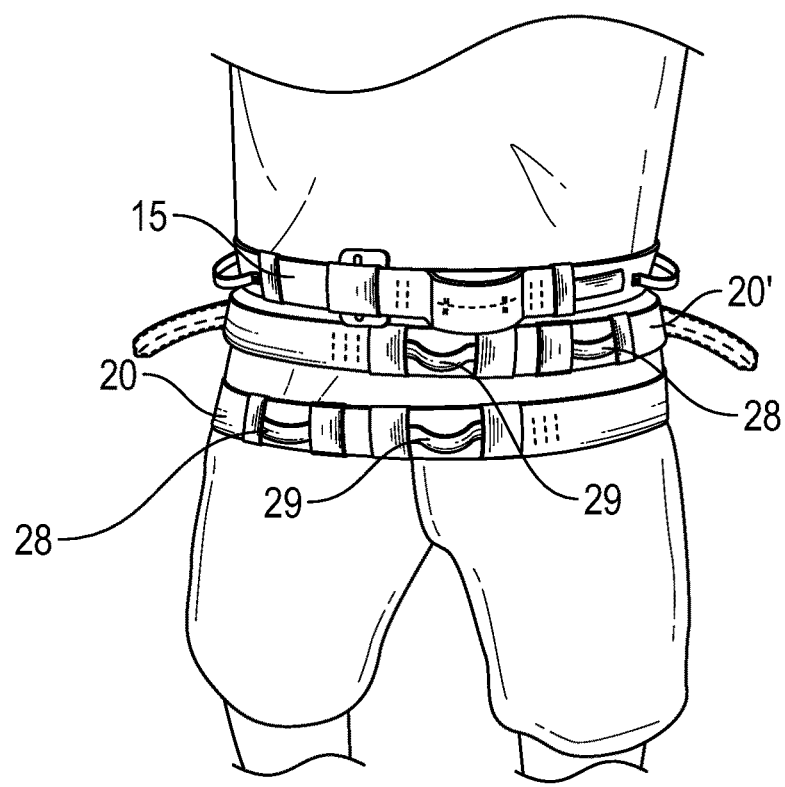
FIG. 12A is a front view of the apparatus and system according to the present invention, with the thigh strap leg loops detached from the main belt and rotated 180° (relative to the view of FIG. 10) to be deployed about the pelvis of a user, and configured for active use as a pelvic binder.
Figure 12B:
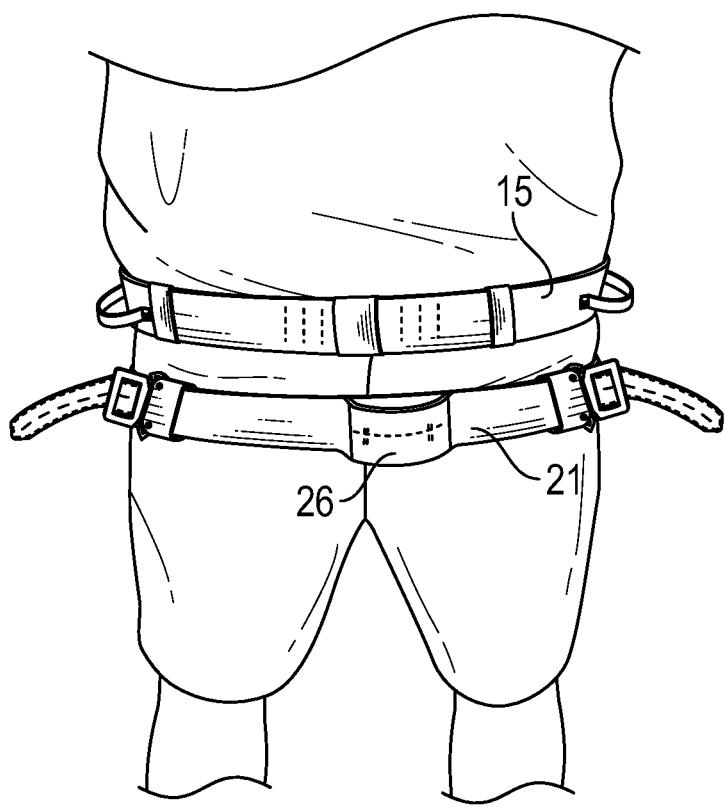
FIG. 12B is a rear view of the apparatus and system according to the present invention, with the thigh strap leg loops deployed about the pelvis of a user, configured for active use as a pelvic binder (as seen also in FIG. 12A)

It is possible for the user to deploy the thigh straps 20, 20' as a pelvic binder on herself in the event of an accident. Combined reference is made to FIGS. 12A and 12B, showing the repositioning of the looped thigh straps 20, 20' upon the user herself for use as a pelvic binder. However, the use of the apparatus upon another person, besides the user, is executed in a substantially similar manner, and a person skilled in the art understands that the person seen in FIGS. 12A, 12B, and 13-15 may be a second-person patient; the thigh straps 20, 20' (but not the main belt 15) are removed from the user and placed upon the patient in the manner of FIGS. 12A and 12B, and FIGS. 13 and 14. To reposition the thigh strap leg loops 20, 20' for use as a pelvic binder, the user unclips the belay device or carabiner 30 to disconnect the leg loops from the main belt 15. The strap leg loops 20, 20' are then rotated 180° upon the patient's body to relocate the carabiner loop 26 centered at the user's back, as seen in FIG. 12A, and particularly FIG. 12B. The two distinct loops 20, 20' are now positioned at the front of the patient's pelvis (FIG. 12A), while their single connecting portion 21 is near the buttocks (FIG. 12B). The two strap leg loops 20, 20' are then separated vertically, so that they are no longer overlying one upon the other (i.e., as in FIGS. 10, 11). This vertical separation, seen best in FIG. 12A, allows one strap loop 20 to be placed around a lower portion of the pelvis, and the other strap loop 20' to be placed around a more upper portion of the pelvis, as seen in FIG. 12A.

Figure 13:
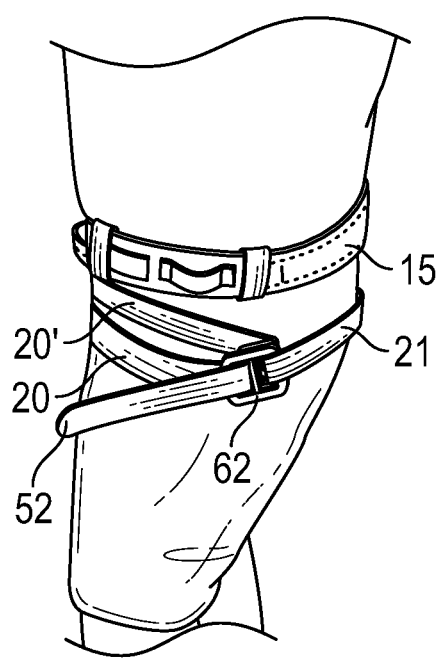
FIG. 13 is a left side view of the apparatus and system according to the present invention, with the thigh strap leg loops deployed about the pelvis of a user, configured for active use as a pelvic binder.
Figure 14:
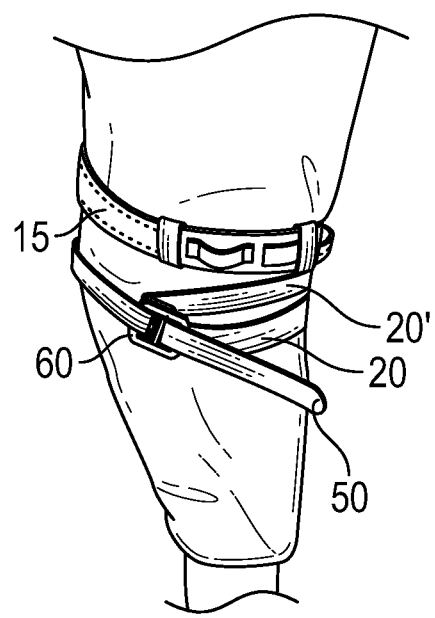
FIG. 14 is a right side view of the apparatus and system according to the present invention, with the thigh strap leg loops deployed about the pelvis of a user, configured for active use as a pelvic binder.

Consideration of FIGS. 13 and 14 discloses how, in the pelvic binder configuration, the strap connecting portion 21 is situated laterally and medially across the back of the pelvis, while a first strap loop (either 20 or 20', the first loop is element 20' in the figures) is laterally on the upper portion of the patient's pelvis and the second strap loop (either 20' or 20, correspondingly, loop 20 seen in the figures) is below the first strap loop. In this manner, the practice of the invention can compress and stabilize the pelvis by applying pressure at different, separated vertical elevations (relative to the pelvic girdle).

Figure 15:
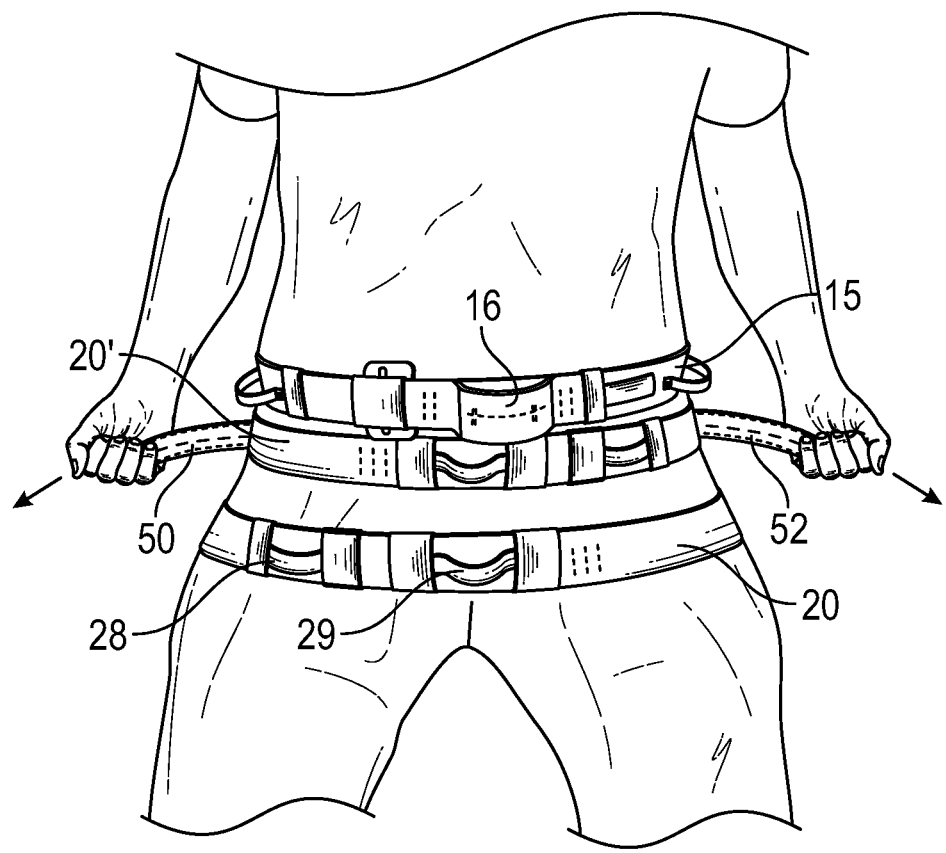
FIG. 15 is a front view of the apparatus and system according to the present invention, with the thigh strap leg loops deployed about the pelvis of a user, configured for active use as a pelvic binder, showing the user pulling on free ends of the leg loop straps to tighten the pelvic binder.

The thigh strap loops 20, 20' may then be used to apply a reasonably uniform circumferential compression to the pelvic girdle, as indicated with reference to FIG. 15. With the thigh strap leg loops 20 and 20' positioned upon the patient as seen in FIGS. 12A though 14, the respective free ends 50, 52 of the looped straps are available for gripping in the user's (or patient's) hands, as seen in FIG. 15. The user then pulls outward on the free ends 50, 52 of the straps, as indicated by the two directional arrows in FIG. 15. This pulling action by the user causes the corresponding strap to controllably and frictionally slide through the ladder glide portion of the respective binder adjustment buckle 60 or 62, (or 22, 22' in the embodiment of FIGS. 2-6), resulting in a reduction in the effective circumference of each strap loop 20, 20'. This in turn imparts the remedial compressive force to the pelvis. The consequent compression desirably stabilizes the injured pelvis, and may ease pain and reduce possible internal hemorrhaging.

Figure 16A:
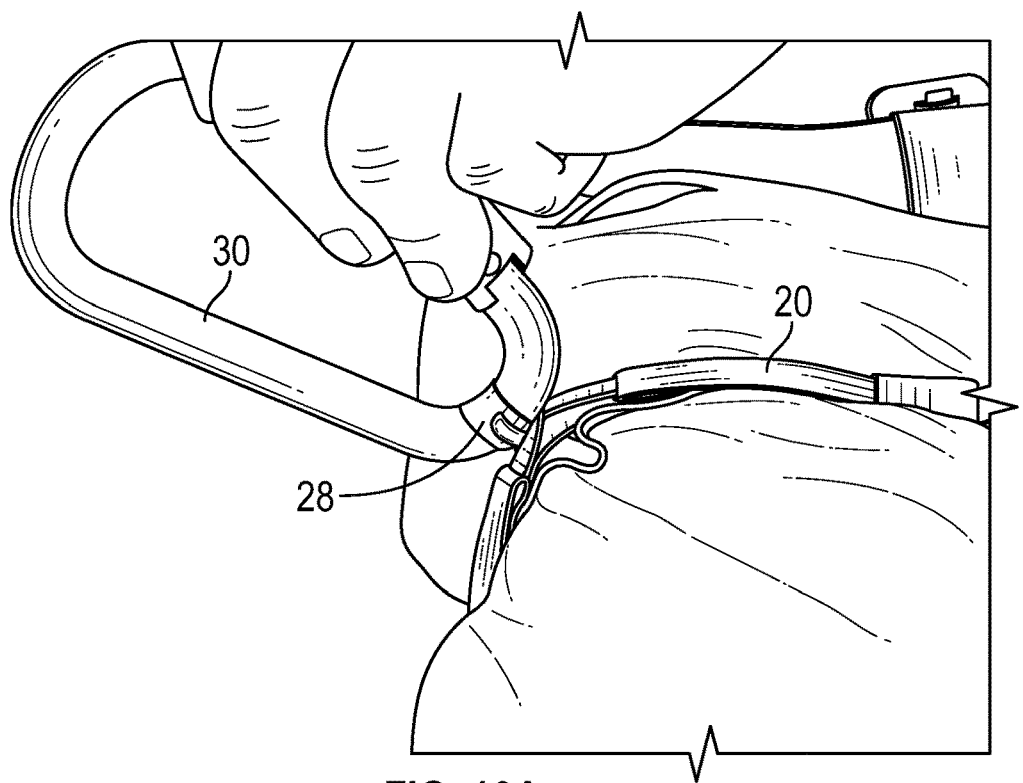
FIG. 16A is an enlarged view of a torsion tool disposed through an optional holder loop and twisted to tighten a thigh strap leg loop to provide supplemental compressive force in an alternative embodiment of the apparatus system configured as a pelvic binder.
Figure 16B:
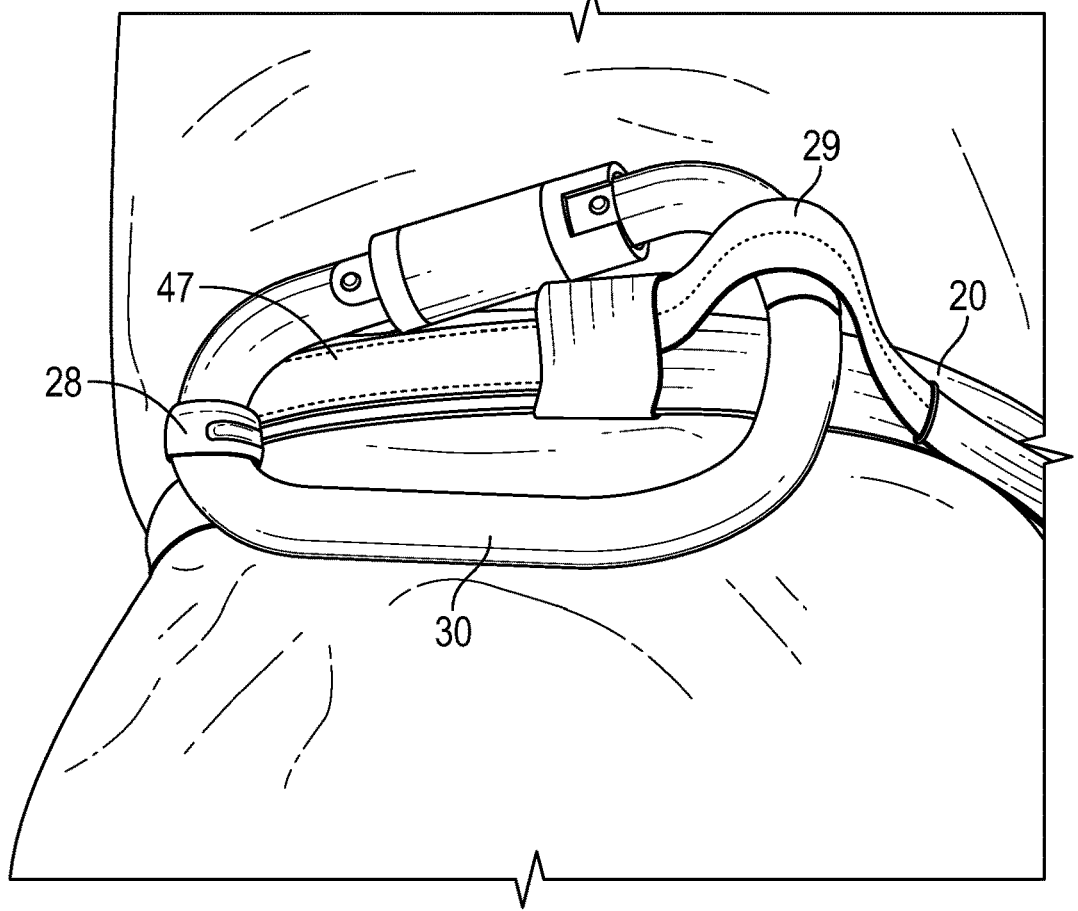
FIG. 16 B is an enlarged view of the torsion tool seen in FIG. 16A, shown additionally disposed through an optional autoblock loop to maintain the twisted condition of the holder loop to provide supplemental compressive force in an alternative embodiment of the apparatus system configured as a pelvic binder.

Another, optional, aspect of the invention is now disclosed. As seen, for example, in FIGS. 12A and 15, the each of the thigh straps 20, 20' is provided with a holder loop 28 and an autoblock loop 29. Thigh straps provided with holder loops and autoblock loops are described in additional detail in my co-pending U.S. patent application Ser. No. 15/255,427, filed 2 Sep. 2016 (now U.S. Pat. No. 10,765,437), the entirety of which is incorporated herein by reference. A windlass device, such as the carabiner 30 can be used with a holder loop 28 and an autoblock loop 29 on the loop of a thigh strap 20 to permit additional compressive forces to be applied to the patient's pelvis. FIG. 16A illustrates that a carabiner 30 can be exploited as a windlass to be disposed through the holder loop 28 on a looped thigh strap 20, and to twist the holder loop. FIG. 16B, related to the view of FIG. 16A, shows a portion of the binder thigh strap 20 of the system according to the present disclosure, showing the step of fully engaging the windlass carabiner 30 with the second, autoblock, loop 29 on the thigh strap, thereby to maintain and secure the thigh strap in use in the pelvic binder.

As illustrated by consecutive reference to FIGS. 16A and 16B, after the user disposes the carabiner 30 or other torsion tool through the holder loop 28 on the binder leg loop 20, the user grasps the torsion tool 30 and manually rotates it around an imaginary axis of rotation oriented generally oblique to the body of the binder thigh strap 20. The tool or carabiner 30 is then rotated the requisite number of times in the user's judgment to shorten the effective length of the holder loop 28, thereby to constrict the binder thigh strap 20 to further compress the pelvis. Such rotation shortens the effective length of the strip of the carabiner holder loop 28; consequently, the effective circumferential length of the overall loop of the binder thigh strap 20 likewise is shortened, resulting in the application of supplemental compressive force to the pelvis via the looped binder thigh strap 20.

It is then desirable to have some means to maintain the torsion tool or carabiner 30, in position. The torsion item or windlass carabiner must not be allowed non-deliberately to counter-rotate, which would release partially the pelvic binder's constricted condition. In this embodiment, the position of the windlass carabiner 30 is maintained in compressive position by the advantageous engagement of the carabiner with the second, autoblock, loop 29. Most basically, this engagement may simply be the act of inserting a portion of the torsion item into the autoblock loop. In the preferred embodiment, this engagement of the torsion item with the second loop is the act of clipping of the carabiner 30 to the nearby second loop, e.g., the second, autoblock, loop 29. This step of clipping the carabiner 30 to a second loop 29 is shown in FIG. 16B. Thus clippably engaged with the autoblock loop 29, the windlass carabiner 30 is maintained in its "tightened" position to maintain the constricted condition of the binder thigh strap 20 placed circumferentially around the patient's pelvis. The user thus is freed from the need to hold manually the carabiner 30 in position for continued application of supplemental binder pressure. Accordingly, a carabiner 30 that has been taken from the handy location on the harness belt 15 or thigh strap 20 is held in position for as long as medically indicated to maintain the function of the pelvic binder. The user's hands are freed for use on other urgent tasks further to obtaining medial help for himself or his patient including evacuation to a first aid station or hospital.

A method according to this disclosure accordingly includes several steps. In summary, a climbing harness system includes a thigh straps portion and a harness belt portion. Two thigh strap portions are connectable, as with a carabiner, to a main carabiner loop on the harness belt portion to provide a sitting harness system. Upon encountering the need for an emergency pelvic binder, the user detaches the dual thigh straps from the harness belt. The method then includes disengaging the first male part from the first female part of a juncture buckle in a first thigh strap, and disengaging the second male part from the second female part of a second juncture buckle in a second thigh strap. The open strap loops are then nearly closed to define two new strap loops in concentric co-registration, with the first male part proximal to the second female part, and the second male part proximal to the first female part, of the disengaged juncture buckles. The two new strap loops thus defined are wrapped around the patient's pelvis, and the first male part is engaged with the second female part, while the second male part is engaged with the first female part to define two closed strap loops encircling the injured pelvis. The two newly defined loops are then adjustably tightened to provide therapeutic compression on the patent to stabilize her pelvis according to traumatic pelvis injury treatment protocols known in the emergency medical arts.

Although the invention has been described in detail with particular reference to these preferred embodiments, other embodiments can achieve the same results. The present inventive method can be practiced by employing generally conventional materials and equipment. Accordingly, the details of such materials and equipment are not set forth herein in detail. In this description, specific details are set forth, such as specific materials, structures, processes, etc., in order to provide a thorough understanding of the present invention. However, as one having ordinary skill in the art would recognize, the present invention can be practiced without resorting strictly only to the details specifically set forth. In other instances, well known processing structures have not been described in detail, in order not to unnecessarily obscure the present invention.

Only some embodiments of the invention and but a few examples of its versatility are described in the present disclosure. It is understood that the invention is capable of use in various other combinations and is capable of changes or modifications within the scope of the inventive concept as expressed herein. Modifications of the invention will be obvious to those skilled in the art and it is intended to cover in the appended claims all such modifications and equivalents.

I claim:

1. A method for combining a climbing harness and pelvic binder comprising releasably connecting a thigh straps portion to a harness belt portion to provide a sitting harness, and further comprising:
   providing the thigh straps portion with two thigh strap loops, each strap loop having an effective circumference and a free end;
   engaging the free end of each strap loop through a respective one of at least two adjustment buckles;
   releasably disposing the thigh straps portion and the harness belt portion about a user's waist;
   upon encountering a need for an emergency pelvic binder, disconnecting the thigh straps portion from the harness belt portion;
   adjusting the effective circumference of each of the thigh strap loops to be greater than the circumference of a patient's pelvis;
   placing both thigh strap loops circumferentially around the patent's pelvis; and
   pulling upon the free ends of the thigh strap loops to actuate the adjustment buckles to reduce the effective circumference of each thigh strap loop;
   thereby applying circumferentially a compressive force to stabilize the patent's pelvis.

2. The method according to claim 1, further comprising providing each of the looped straps with an associated junction buckle, each junction buckle having a male part yet releasably engageable with a female part.

3. The method according to claim 1, further comprising the steps of:
   providing at least one of the thigh straps with a holder loop;
   after the step of placing both thigh strap loops circumferentially around the patent's pelvis, disposing a windlass torsion tool through the holder loop; and
   manually rotating the torsion tool to shorten the effective length of the holder loop, thereby constricting the thigh strap to apply supplemental compressive force to the pelvis via the looped thigh strap.

4. The method according to claim 3, further comprising the steps of: providing the at least one of the thigh straps with an autoblock loop; and after manually rotating the torsion tool to shorten the effective length of the holder loop, engaging the torsion tool with the autoblock loop to maintain the shortened effective length of the holder loop.

* * * * *